(12) United States Patent
Gueret (10) Patent No.: US 6,623,751 B2
(45) Date of Patent: *Sep. 23, 2003

(54) COSMETIC, PHARMACEUTICAL, OR DERMATOLOGICAL PATCH

(75) Inventor: Jean-Louis H. Gueret, Paris (FR)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/362,680

(22) Filed: Jul. 29, 1999

(65) Prior Publication Data

US 2001/0007671 A1 Jul. 12, 2001

(30) Foreign Application Priority Data

Jul. 30, 1998 (FR) .............................. 98-09794
Jul. 30, 1998 (FR) .............................. 98-09795
Jul. 31, 1998 (FR) .............................. 98-09880

(51) Int. Cl.$^7$ ..................... A61F 13/00; A61K 31/74; A61L 15/16
(52) U.S. Cl. ..................... 424/449; 424/443; 424/448; 424/400; 424/78.02
(58) Field of Search ................. 424/449, 443, 424/448, 401, 78.3

(56) References Cited

U.S. PATENT DOCUMENTS

| 3,428,043 A | | 2/1969 | Shepherd | |
|---|---|---|---|---|
| 3,499,446 A | * | 3/1970 | Tsuneizumi et al. | ........ 128/260 |
| 4,377,160 A | | 3/1983 | Romaine | |
| 4,585,797 A | * | 4/1986 | Cioca | ........................ 514/773 |
| 4,631,227 A | * | 12/1986 | Nakamura | .................. 428/283 |
| 4,643,939 A | | 2/1987 | Sugiyama et al. | |
| 4,814,167 A | | 3/1989 | Wirth et al. | |
| 5,026,552 A | * | 6/1991 | Gueret et al. | ................ 424/401 |
| 5,100,672 A | | 3/1992 | Gueret et al. | |
| 5,232,707 A | | 8/1993 | Lokensgard | |
| 5,374,429 A | * | 12/1994 | Kinoshita et al. | ........... 424/448 |
| 5,466,456 A | | 11/1995 | Glover | |
| 5,466,724 A | | 11/1995 | Volke et al. | |
| 5,512,277 A | * | 4/1996 | Uemura et al. | .......... 424/79.03 |
| 5,785,978 A | * | 7/1998 | Porter et al. | |
| 5,811,107 A | | 9/1998 | Gangadharan et al. | |
| 5,958,443 A | * | 9/1999 | Viegas et al. | ................ 424/427 |
| 6,039,967 A | * | 3/2000 | Ottoboni et al. | |
| 6,153,176 A | * | 11/2000 | Kaleta et al. | |
| 6,180,122 B1 | * | 1/2001 | Roulier et al. | |

FOREIGN PATENT DOCUMENTS

AU 206 114 11/1989

(List continued on next page.)

OTHER PUBLICATIONS

English language Derwent Anstract of DE 44 46 380.
English language Derwent Anstract of EP 0 764 441.
English language Derwent Anstract of FR 2 276 030.
English language translation of FR 2 515 651.
English language translation of FR 2 538 247.
English language Derwent Anstract of FR 2 738 744.
English language Derwent Anstract of FR 2 750 050.

*Primary Examiner*—Thurman K. Page
*Assistant Examiner*—Isis Ghali
(74) *Attorney, Agent, or Firm*—Finnegan, Henderson, Farabow, Garrett & Dunner, LLP (57) ABSTRACT

A cosmetic, pharmaceutical, or dermatological patch includes a composition including a hydrophilic gelling system in an aqueous phase. The hydrophilic gelling system includes at least one gellan gum and at least one other hydrocolloid.

71 Claims, 4 Drawing Sheets

FOREIGN PATENT DOCUMENTS

| | | | |
|---|---|---|---|
| DE | 44 46 380 | 1/1996 | |
| EP | 0 063 875 | 11/1982 | |
| EP | 0 190 814 | * 1/1986 | ........... A61L/15/06 |
| EP | 0 190 814 | 8/1986 | |
| EP | 0 309 309 | 3/1989 | |
| EP | 0 412 869 | 2/1991 | |
| EP | 0 651 984 | 5/1995 | |
| EP | 0 764 441 | 3/1997 | |
| FR | 2 276 030 | 1/1976 | |
| FR | 2 515 651 | 3/1983 | |
| FR | 2 538 247 | 6/1984 | |
| FR | 2 738 744 | 3/1997 | |
| FR | 2 750 050 | 12/1997 | |
| GB | 2 265 086 | 9/1993 | |
| WO | WO 87/05206 | 9/1987 | |
| WO | WO 94/02674 | 2/1994 | |
| WO | WO 94/17837 | 8/1994 | |
| WO | WO 94/22423 | 10/1994 | |
| WO | WO 95/05204 | 2/1995 | |
| WO | WO 95/28136 | 10/1995 | |
| WO | WO 96/14822 | 5/1996 | |
| WO | WO 98/31315 | 7/1998 | |
| WO | WO 98/42303 | 10/1998 | |

\* cited by examiner

COSMETIC, PHARMACEUTICAL, OR DERMATOLOGICAL PATCH

The present application refers to U.S. patent application Ser. No. 09/362,681 filed on Jul. 29, 1999 and U.S. patent application Ser. No. 09/363.171, filed on Jul. 29, 1999. The disclosure of these applications is incorporated herein by reference.

The present invention relates to a cosmetic, pharmaceutical, or dermatological patch. The patch preferably provides a treating, refreshing, or relaxing action. The patch provides a cosmetic and/or pharmaceutical effect by bringing at least one active substance dispersed on the patch in contact with the skin. The patch may be applied to the skin from a few minutes to an hour or more, depending on the type of treatment for which the patch is used.

Conventional patches are generally manufactured by applying a solution including one or more active agents to a sheet of material and allowing the solution to dry. The dried sheet is then cut into different shapes and sizes, depending on the intended use for the patch. After cutting the patch to the desired shape and size, the patch is packaged in a sealed package.

Conventional manufacturing techniques suffer from several drawbacks. For example, the method of preparing patches described above requires complex layering machines and results in large losses of preparation materials (i.e., sheet material and solution). Manufacturing waste is particularly large when the shape of the patch is complex, such as patches specifically designed to fit on different parts of the face (e.g., nose, corner of the eye, forehead, etc.). Also, the manufacture of most conventional patches requires an additional step of packaging, thereby increasing the cost of production.

In light of the foregoing, there is a need in the art for an improved patch.

Accordingly, the present invention is directed to a patch that obviates one or more of the short-comings of the related art.

A preferred object of the invention is to provide patches with high water content, into which various active agents may be incorporated, thereby imparting great softness, freshness, and/or coolness to the skin during application. The patches are preferably easily manipulated, especially during application to and/or removal from the skin.

In particular, one objective of the invention is to provide a patch which can be easily manipulated and which, when applied to the skin, provides new sensations, especially coolness and softness.

Another objective of the invention is to produce a patch that is formed directly in situ in its packaging.

Yet another objective of the invention is to produce a patch which is simple and economical to produce.

It should be understood that the invention could still be practiced without performing one or more of the preferred objects and/or advantages set forth above. Still other objects will become apparent after reading the following description of the invention.

To achieve these and other advantages, and in accordance with the purposes of the invention, as embodied and broadly described herein, the invention includes a cosmetic, pharmaceutical, or dermatological patch that includes a composition including a hydrophilic gelling system in an aqueous phase. The hydrophilic gelling system includes a gellan gum and at least one other hydrocolloid.

Although gelled products formed from mixtures of gellan gum and another gum are known in the food industry, those gelled products are not appropriate for cosmetic, dermatological, and pharmaceutical applications, which require structural integrity, strength, and the ability to transfer treatment products to skin.

The patch of the present invention preferably includes a large amount of water so that it is cool upon application, while at the same time giving a strong impression of softness. The patch is preferably applied directly to the skin, without pre-wetting the patch and/or the skin. However, in an alternate embodiment, the patch and/or the skin is pre-wetted prior to application of the patch. The composition is preferably homogeneous and stable, and thus and does not require a particular preparation technique. The composition preferably includes active agents that are easily transferred onto the skin. Preferably, the composition is cool on application and is sufficiently strong for application to and/or removal from the skin. The patch is preferably easily manipulated, in particular, when the patch is applied to and/or removed from the skin.

The term "patch" should be understood to include a structure including one or more layers that can be applied to and/or removed from the skin. The patch preferably includes a composition including a hydrophilic gelling system that forms a layer capable of being applied to and/or removed from the skin. The composition preferably includes at least one active agent configured to interact with the skin, whether by diffusion into the skin (through the dermis) or by surface contact. Preferably, the patch does not disintegrate when it is removed from the skin. At least some of the water and/or active agents in the composition preferably escape from the patch during application of the patch to the skin. For example, the water and/or active agents evaporate into the environment and/or are transferred to the skin. Depending on the type of interaction between the patch and the skin, the application time varies from about a few seconds to about a few hours, or even to about a few days.

In a preferred embodiment, the patch includes a reinforcing member that provides additional structural integrity to the patch. The reinforcing member provides several benefits to the patch. For example, the reinforcing member provides reinforcement to the patch so that it does not become deformed (e.g. elongated) during application. It also facilitates removal of the patch from the container in which it is packaged. It advantageously allows the manufacture of thinner patches because of the additional structural support it provides. It allows the flexibility of the patch to be modified so that the patch will conform to a surface when applied. It further allows the patch to be reused. Moreover, it facilitates manipulation of the patch and can produce an occlusive barrier.

The reinforcing member may be located on the surface of the patch, or it may be embedded within the composition so that the composition forms a matrix about at least a portion of the reinforcing member. Preferably, the reinforcing member is made of woven fabrics, nonwoven fabrics, and perforated films. More preferably, the reinforcing member is a net (e.g., a polyamide net).

In an embodiment, the reinforcing member is a support and the composition is coated on the support. After the coating of the composition on the support, the patch is cut to the desired shape. The coating of the composition to a desired thickness may be carried out by a roll, by a doctor blade, and/or by calendering. The support preferably includes one of woven fabrics, nonwoven fabrics, and perforated plastic films. After the patch has been cut, it is preferably packaged inside a sealed packet.

The term "hydrocolloid" should be understood to mean a water-soluble macromolecule that does not alter the value of the water activity of the composition containing it.

Preferably, the gelling system represents less than 20% of the total weight of the composition. A relatively low proportion of gelling agents allows the composition to avoid leaving a visible deposit when applied to the skin and the patch to be transparent of translucent. The hydrophilic gelling system preferably forms a gelled solid that has a compressive strength greater than or equal to 20 grams at room temperature (i.e., about 20–25° C.). The compressive strength measurements above are preferably obtained by inserting an axisymmetric cylindrical probe having a diameter of 0.8 cm into the gelled solid to a depth of about 1 mm at a rate of about 0.5 mm/s and removing the probe from the gelled solid at a rate of about 0.5 mm/s. The compressive strength is preferably measured using an analyser similar or identical to the "LFRA Texture Analyser" sold by Stevens/Mechtric.

Preferably, the gellan gum is at least about 0.5% of the total weight of the composition. More preferably, the gellan gum ranges from about 2% to about 15% of the total weight of the composition. Even more preferably, the gellan gum ranges from about 2% to about 6% of the total weight of the composition.

The hydrocolloid associated with the gellan gum is chosen from cellulose and its derivatives; seaweed extracts; seed extracts; plant exudates; microorganism exudates; fruit extracts; gelling agents of animal origin; synthetic water-soluble gelling polymers; amphiphilic polymers; silicon derivatives; and their mixtures.

In more detail, the hydrocolloid associated with the gellan gum may be chosen from:

- cellulose and its derivatives such as carboxymethylcellulose, hydroxypropylcellulose, methylcellulose, hydroxypropylmethylcellulose and hydroxyethylcellulose, as well as modified celluloses, especially those modified by grafting of the alkyl group;
- seaweed extracts such as agar agar, carragheenans and alginates;
- seed extracts such as carob gum, guar gum, and modified guar gums, especially those modified by grafting of the alkyl group;
- plant exudates such as gum arabic, karaya gum, gum tragacanth and gatty gum;
- microorganism exudates such as xanthan gum;
- fruit extracts such as pectins;
- gelling agents of animal origin, such as gelatin and caseinates;
- synthetic water-soluble gelling polymers such as crosslinked polyacrylic acids, including those crosslinked via an alkyl chain, such as CARBOPOL and PEMULEN from the company Goodrich;
- silicon derivatives such as synthetic hectorites like the products LAPONITE RD and RDS sold by the company Waverly and aluminium magnesium silicates like the product VEEGUM sold by the company Vanderbilt;
- polymers such as POLYCARE® sold by the company Rhone-Poulenc under the reference PS-20 and PS-32; and
- a mixture of these compounds.

Advantageously, a hydrocolloid chosen from carob gum, xanthan gum, cellulose derivatives, a modified guar gum and mixtures of these compounds may be used in association with the gellan gum. Most particularly xanthan gum, carboxymethylcellulose and modified guar gums are used. The latter may especially be hydroxypropyl guar.

Preferably, the hydrocolloid associated with the gellan gum is present in an amount ranging from 0.5 to 10% and more preferably from 0.5% to 5% of the total weight of the composition.

Advantageously, the aqueous phase represents from 60 to 97% of the total weight of the composition and preferably 80 to 95% of the total weight of the composition.

According to one particular embodiment of the invention, the composition furthermore comprises at least one oil, this addition of oil can provide greater comfort when the composition is applied to the skin.

Representative oils include mineral oils, oils of plant origin, oils of animal origin, synthetic oils such as fatty esters, silicone oils such as volatile silicone oils, polymethylsiloxanes, polymethylphenylsiloxanes, polysiloxanes modified by any of fatty acids, fatty alcohols, and polyoxyalkylenes, fluorinated silicones and perfluorinated oils. Other fatty substances such as fatty acids, fatty alcohols and waxes may be added.

The at least one oil and the other fatty substances optionally present constitute the fatty phase.

The fatty phase may be present in proportions ranging, for example, up to 30%, preferably from 0.1 to 20% and better still from 0.5 to 10% of the total weight of the composition, these proportions varying depending on the application chosen.

The oil may be introduced into the aqueous phase in the presence of at least one surfactant to ensure better dispersion.

The compositions according to the invention may therefore also contain at least one surfactant chosen from nonionic, anionic, cationic, and amphoteric surfactants, normally used in the cosmetic and/or dermatological fields. When it is present, the amount of surfactant preferably varies from 0.05 to 8% and better still from 0.05 to 5% of the total weight of the composition.

It is possible to modify the stiffness of the compositions according to the invention by adding to them at least one salt which will increase this stiffness. These salts may be chosen from monovalent, divalent and trivalent metal salts, and more particularly alkali metal and alkaline-earth metal salts, particularly sodium and calcium salts. The ions making up these salts may be chosen, for example, from carbonates, bicarbonates, sulphates, glycerophosphates, borates, chlorides, nitrates, acetates, hydroxides and persulphates, as well as salts of $\alpha$-hydroxy acids (citrates, tartrates, lactates and malates), salts of fruit acids, and salts of amino acids (aspartates, arginates, glycocholates and fumarates). The amount of salt may range from 0.01 to 2%, preferably from 0.1 to 1%, of the total weight of the composition. The stiffness may also be modified by the presence of at least one alcohol.

Preferably, the salt is chosen from calcium, magnesium and strontium nitrate, calcium and magnesium borate, calcium, sodium, magnesium, strontium, neodymium, and manganese chloride, magnesium and calcium sulphate, calcium and magnesium acetate and their mixtures. Salts may also be incorporated so as to retard the setting of the gel, which setting may occur after a time ranging from 30 seconds to 24 hours.

Apart from water, the composition (P) may include at least one solvent chosen from primary alcohols such as ethanol and isopropanol, glycols such as propylene glycol, butylene glycol, dipropylene glycol and diethylene glycol, glycol ethers such as monopropylene, dipropylene and tripropylene glycol alkyl($C_1$–$C_4$)ethers, monoethylene, diethylene and triethylene glycol and their mixtures. These solvents may represent 10% by weight of the composition.

The composition (P) preferably includes at least one active agent having an effect on the skin, such as antioxidants, free-radical scavengers, moisturizers, bleaching agents, liporegulators, anti-acne agents, antiseborrhoeic agents, anti-ageing agents, softeners, anti-wrinkle agents, keratolytic agents, anti-inflammatories, refreshing agents, cicatrizing agents, vascular protective agents, antibacterials, antifungals, antiperspirants, deodorants, skin conditioners, desensitizing agents, immunomodulators and nourishing agents, or moisture absorbers (cotton, polyacrylate) and sebum absorbers (Orgasol).

The composition (P) may include at least one water-soluble active agent chosen from ascorbic acid and its biologically compatible salts, enzymes, antibiotics, components having a tautening effect, α-hydroxy acids and their salts, hydroxylated polyacids, sucroses and their derivatives, urea, amino acids, oligopeptides, water-soluble plant and yeast extracts, protein hydrolysates, hyaluronic acid, mucopolysaccharides, vitamins $B_2$, $B_6$, H and PP, panthenol, folic acid, acetylsalicylic acid, allantoin, glycyrrhetic acid, kojic acid and hydroquinone.

The composition P may further include at least one liposoluble compound chosen from D-α-tocopherol, DL-α-tocopherol, D-α-tocopherol acetate, DL-α-tocopherol acetate, ascorbyl palmitate, vitamin F and vitamin F glycerides, vitamins D, vitamin $D_2$, vitamin $D_3$, retinol, retinol esters, retinol palmitate, retinol propionate, β-carotene, D-panthenol, farnesol, farnesyl acetate; jojoba and blackcurrant oils rich in essential fatty acids; keratolytic agents such as salicylic acid, its salts and its esters, 5-(n-octanoyl)salicylic acid and its esters, alkyl esters of α-hydroxy acids such as citric acid, lactic acid, glycolic acid; asiatic acid, madecassic acid, asiaticoside, total extract of centella asiatica, β-glycyrrhetinic acid, α-bisabolol, ceramides such as 2-oleoylamino-1,3-octadecane; phytanetriol, milk sphingomyelin, phospholipids of marine origin, rich in polyunsaturated essential fatty acids, ethoxyquin; extract of rosemary, extract of melissa, quercetin, extract of dried microalgae and steroidal anti-inflammatories.

In another aspect, the patch includes pigment selected to allow visualization of at least one of impurities and residues taken from skin when the patch is applied to and/or removed from skin. The use of pigment is preferably for patches that provide a cleansing action that contain, for example, sebum absorbers, since it provides the user with feedback regarding the frequency and nature of the treatment being performed.

In one embodiment, the patch is colored by incorporating synthetic, mineral, and/or organic pigments into the patch. The pigments may include pigments used in the food sector or in cosmetics, for example, pigments for lipsticks and nail varnishes. For example, the patch could be constructed identical to or similar to one or more of the patches disclosed in U.S. application Ser. No. 09/240,603, filed Feb. 1, 1999, the disclosure of which is incorporated herein by reference. By way of example, the pigments may include synthetic pigments or mineral pigments, for example, zirconium oxide or cerium oxide pigments, as well as iron oxide or chromium oxide, and ferric blue, and combinations thereof. Organic pigments can be used, in particular carbon black and barium, strontium, calcium (DC Red No. 7) and aluminium lakes. Preferably, a pigment bearing the reference DC Violet 2 K7014 sold by Kohnstamm® is used.

In another aspect, the invention includes a packaged patch system. The packaged patch system includes a container having an interior, a first end, and a second end opposite to the first end. The first end includes a base portion and the second end includes an opening. The system also includes a cosmetic, pharmaceutical or dermatological patch in the container. The patch is preferably similar to or identical to the patches described above. The system further includes a removable cover sealably closing the opening in the second end.

The patch is preferably formed in a container that can be used as the final packaging for the patch (i.e., the packaging in which the patch is sold). By forming the patch in the final packaging, fewer operations and manipulations are required for the manufacture of this patch than is necessary for many conventional patches. Further, the patch of the present invention can be manufactured to different shapes and sizes for various applications, without the need to cut the patch to the desired shape and size after manufacturing. Thus, the patch of the present invention does not suffer from waste of preparation materials like many conventional patches.

The container is preferably formed by thermoforming or thin-wall injection-molding. A material or a complex of materials that are impervious to oxygen and water vapor are preferably used. The chosen material should be able to withstand manufacturing temperatures of up to 100° C.

The container is preferably formed from a thermoplastic material chosen from polyethylenes or polypropylenes, or from a complex of thermoplastic materials, such as a polyethylene terephthalate/aluminium/polyethylene laminate, or elastomers, in particular silicone elastomers, or thermoplastic elastomers. Making the container out of an elastically deformable material advantageously facilitates removal of the patch from the container.

Preferably, the second end of the container includes a rim defining the opening in the second end and the removable cover is on the rim. For example, the removable cover is attached to the rim by one of bonding, heat-sealing, and welding.

In a preferred embodiment, the removable cover is a protective cap formed from a metallic material (e.g., aluminium), a thermoplastic material, such as a polyethylene or polypropylene, a ceramic, or a combination of such materials. The removable cover is preferably made of materials having a relatively low tendency to adhere to the container. Preferably, the removable cover is welded to the container to assure a good seal.

Preferably, the container includes a breakable corner to facilitate removal of the cover from the container. For example, when the container includes a rim, the breakable corner is a portion of the rim that has the removable cover attached thereto.

In an alternate embodiment, the composition is placed in the container via an opening in the base portion. The opening in the base portion is preferably sealably closed by a cover member after the placing of the composition in the container. For example, the cover member is a protective cap or an adhesive pellet that is bonded or welded to the base portion.

When the composition is placed in the container via the opening in the base portion and the patch includes a reinforcing member, the reinforcing member is preferably located distal to the base portion of the container. Alternatively, when the composition is placed in the container via the opening in the second end, the reinforcing member is located proximal to the base portion of the container. In another embodiment, a first portion of the composition is placed in the container prior to the placing of the reinforcing member and a second portion of the composition is placed in the container after the placing of reinforcing member. Placing the reinforcing member between the first and second portions of composition allows the reinforcing member to be embedded in the composition so that the composition forms a gelled matrix about the reinforcing member.

The composition is preferably at a temperature of about 90° C. when the composition is placed in the container. The setting or gelation of the composition preferably takes place at about 60 to 70° C. Although not preferred, the composition can be placed in the container while it is at a temperature that allows setting of the composition. The setting/gelling may occur during cooling of the composition and/or by a reaction involving water in the composition.

Besides the structural arrangements set forth above, the invention could include a number of other arrangements and procedural steps, such as those explained hereinafter. It is to be understood that both the foregoing general description and the following detailed description are exemplary, and are intended to provide further explanation of the invention as claimed.

The accompanying drawings are included to provide a further understanding of the invention and are incorporated in and constitute a part of this specification. The drawings illustrate embodiments of the invention and, together with the description, serve to explain the principles of the invention. In the drawings.

Reference will now be made in detail to the present preferred embodiments of the invention, examples of which are illustrated in the accompanying drawings. Wherever possible, the same reference numbers are used in the drawings and the description to refer to the same or like parts. In addition, alphabet suffixes on reference numerals are used to refer to similar parts.

Figure 1:
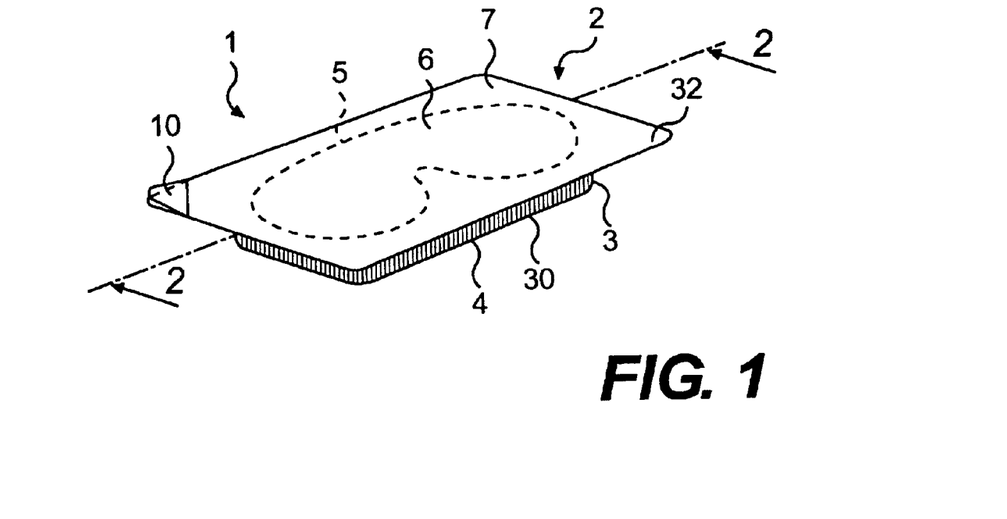
FIG. 1 shows a first embodiment of a packaged patch system.
Figure 6:
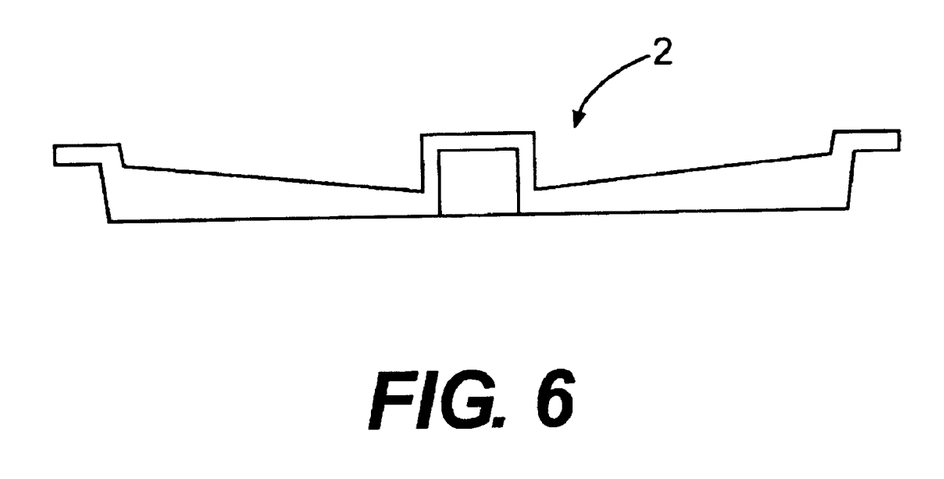
FIG. 6 shows a schematic cross-sectional view of a second embodiment of a packaged patch system including a container having a non-uniform depth.

As shown in FIGS. 1 and 2A–2C, a packaged patch system 1 includes a container 2 formed by thermoforming or thin-wall injection-molding a material, such as a polypropylene. The container 2 includes an interior 3, a first end 30, and a second end 32. The first end 30 includes a base portion 4 and the second end 32 includes an opening 5. Preferably, the interior 3 of the container 2 has a shape capable of forming a patch 11 in the interior 3 of the container 2. Although the depth of the container 2 is preferably at least substantially uniform along the base portion 4, the depth of the container 2 could be non-uniform along the base portion 4, as shown in FIG. 6. As shown in FIG. 1, for example, the patch 11 is preferably configured in the shape of a mask having a cut-out for the bridge of the nose, for treatment of skin around the eyes.

Figure 7:
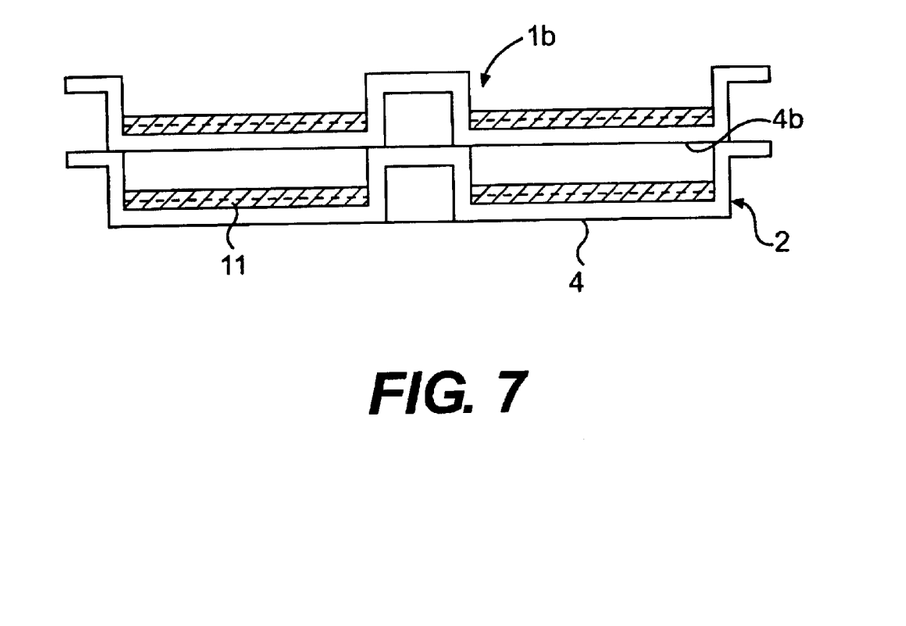
FIG. 7 shows a schematic cross-sectional view of a third embodiment including a stacked arrangement of packaged patch systems.
Figure 8:
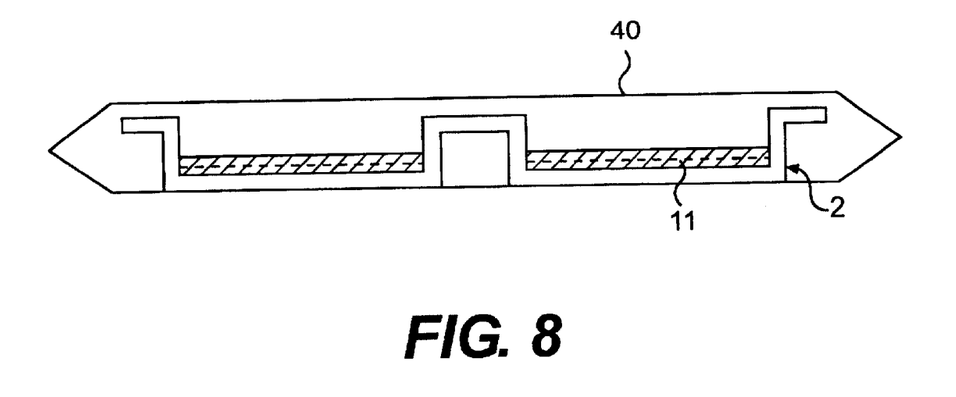
FIG. 8 shows a schematic cross-sectional view of a fourth embodiment of a packaged patch system including a package sealably containing the system.

The opening 5 is sealably covered by a removable cover 6. The removable cover 6 is preferably a heat-sealed protective cap formed of a polypropylene/aluminium/polyethylene complex. In an alternate embodiment (shown in FIG. 8), the removable cover is a portion of a package 40 containing the system 1. In still another embodiment (shown in FIG. 7), the removable cover is a base portion 4b of a second patch packaging system 1b. In the embodiment shown in FIG. 7, there are a series of systems stacked on top of each other, with the base portion of each system (other than the bottom system) functioning as a removable cover for the system located immediately below the respective base portion. The stack of systems is preferably contained in a sealed package (not shown).

Figure 2A:
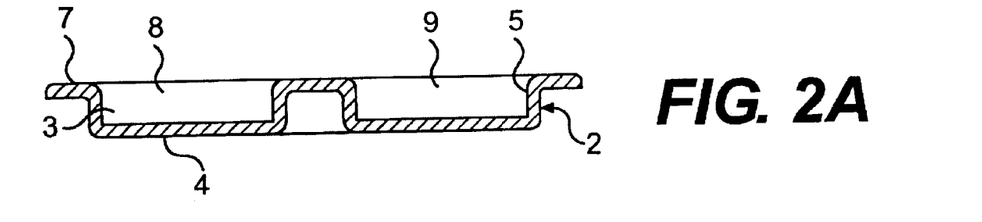
FIGS. 2A, 2B, and 2C show an embodiment of a method for manufacturing the packaged patch system of FIG. 1.
Figure 2B:
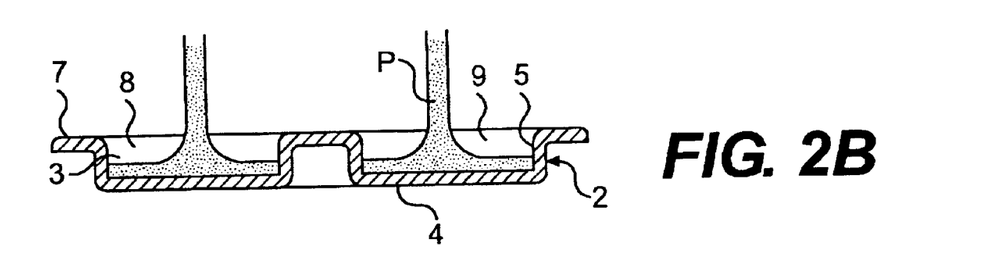
Figure 2C:
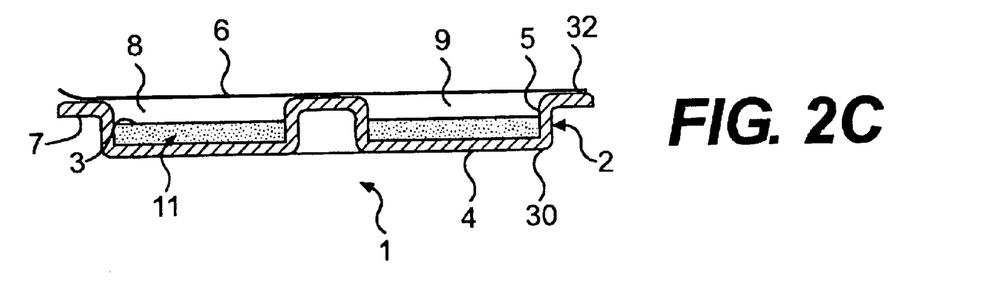

As shown in FIG. 2C, the second end 32 of the container 2 preferably includes a rim 7 defining the opening 5. The removable cover 6 is preferably attached to the rim 7 by one of bonding, heat sealing, and welding.

In a preferred embodiment, the container 2 includes a breakable corner 10, shown in FIG. 1, to facilitate removal of the removable cover 6 from the rim 7, thereby facilitating removal of the patch 11 from the interior 3 of the container 2.

FIGS. 2A–2C show cross-sectional views taken along the line 2—2 of FIG. 1, of various stages in the manufacture of the packaged patch system 1. As shown in FIG. 2A, the container 2 is positioned so that the base portion 4 is below the opening 5 (e.g., the base portion 4 is on a surface). As shown in FIG. 2B, a liquid composition P is placed in the container 2. The composition P is preferably placed in the container 2 at a temperature ranging from about 80° C. to about 90° C. Preferably, the composition P is placed in the container 2 through the opening 5 using two spouts (not shown) located adjacent to a first zone 8 and a second zone 9, respectively, of the interior 3 of the container 2.

As the composition P cools, the composition P preferably sets or gels to form the patch 11. (See FIG. 2C.) Preferably, the patch 11 has a shape and a size of at least a portion of the interior 3 of the container 2. More preferably, the size and shape of the patch is the same as at least a lower portion of the interior 3 of the container 2. In a preferred embodiment, the setting or gelling of the composition P takes place at a temperature of about 60° C. to about 70° C. After the placing of the composition P in the container 2, the opening 5 is preferably closed with the removable cover 6. The removable cover 6 can be placed on the container 2 before, during, or after the setting/gelling of the composition P.

The setting/gelling of the composition P results from the lowering of the temperature of the composition P and/or from an internal reaction within the composition, due at least in part to water contained in the composition.

The patch 11 preferably contains at least one active ingredient capable of performing a cosmetic and/or pharmaceutical treatment to skin when the patch 11 is applied to skin.

Figure 3A:
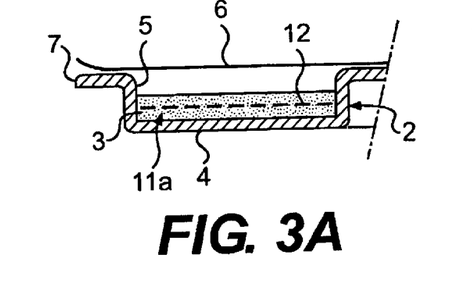
FIGS. 3A, 3B, and 3C show variations of the method shown in FIGS. 2A–2C for manufacturing a packaged patch system.
Figure 3B:
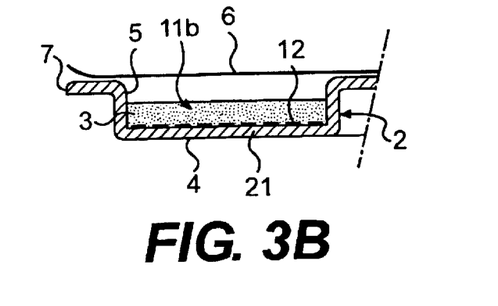
Figure 3C:
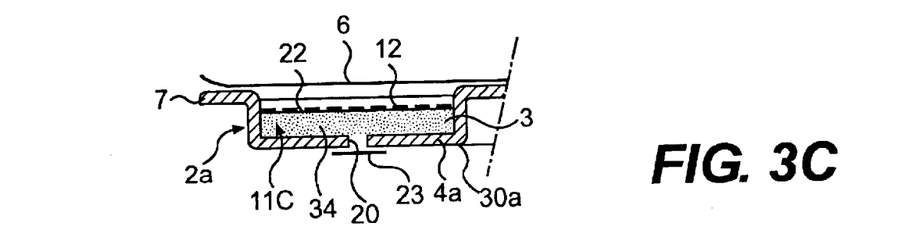

FIGS. 3A–3C show variations of the method shown in FIGS. 2A–2C and described above. For example, as shown in FIG. 3A, a reinforcing member 12 is located in a middle portion of the patch 11a. The patch 11a is formed by placing a first portion of the composition P in the container 2 and then placing the reinforcing member 12 in the container 2. Thereafter, a second portion of the composition P is placed in the container 2 over the reinforcing member 12 to sandwich the reinforcing member 12 between the layers of the gelled matrix. This configuration allows the thickness of the patch 11a to be minimized, while still retaining sufficient structural integrity to perform a treatment.

Preferably, the thickness of the patch ranges from about a few tenths of a millimeter to about a few millimeters. The preferred thickness for the patch depends on the desired application surface or treatment. The reinforcing member 12 preferably has a thickness ranging from between about 0.01 mm to about 2 mm. The mass per unit area of the reinforcing member 12 preferably ranges from about 5 to 60 g/m². More preferably, the mass per unit area of the reinforcing member 12 ranges from about 10 to 40 g/m².

Figure 5:
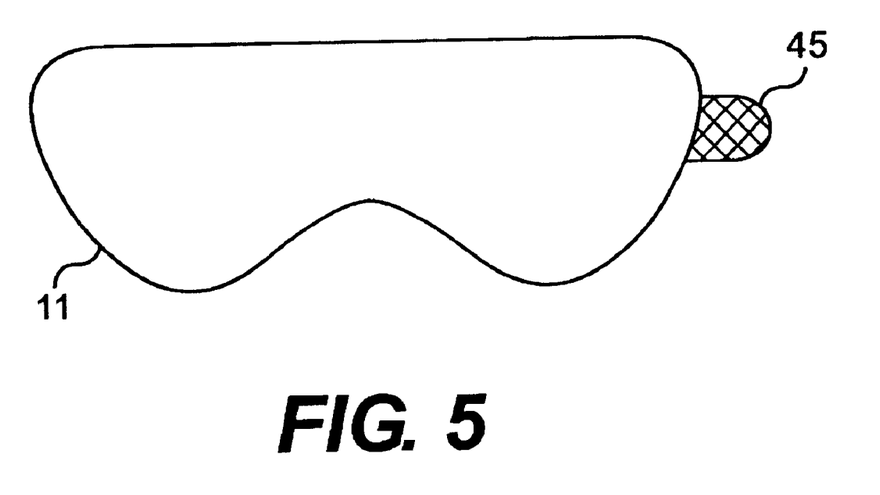
FIG. 5 shows a schematic view of a patch having a portion of a reinforcing member extending from the patch.

As shown in FIG. 5, a portion 45 of the reinforcing member 12 optionally extends from the patch 11 and is not covered by the composition P. The portion 45 advantageously provides a grip to facilitate removal of the patch 11 from the container 2.

As shown in FIG. 3B, the reinforcing member 12 is placed in the container 2 prior to the placing of the composition P in the container 2 so that the reinforcing member 12 is located in a portion 21 of the patch 11b proximal to the base portion 4.

Figure 4A:
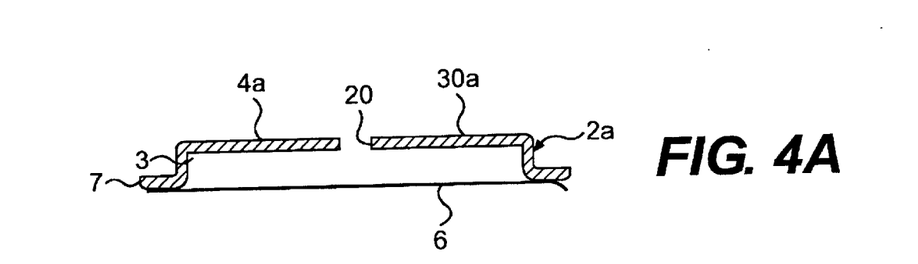
FIGS. 4A, 4B, and 4C show an alternate method for manufacturing a packaged patch system.
Figure 4B:
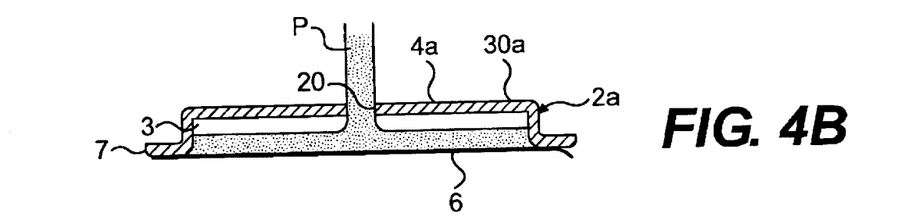
Figure 4C:
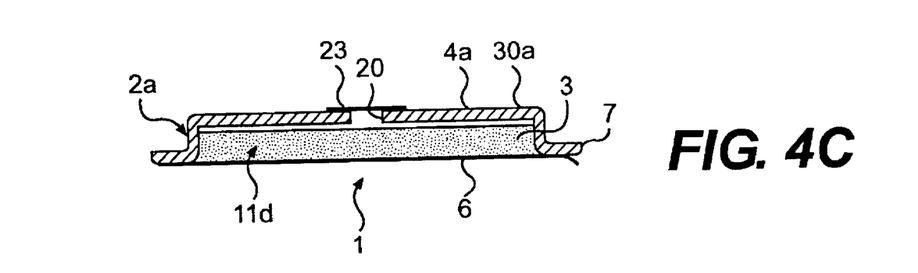

FIGS. 3C and 4A–4B show alternate methods of manufacturing patches 11c, 11d. The embodiments of FIGS. 3C and 4A–4B are similar, except that the embodiment of FIG. 3C includes the reinforcing member 12 while the embodiment of FIGS. 4A–4B does not. In both of these embodiments, rather than placing the composition P in the container 2 through the opening 5 in the second end 32, the composition P is placed in a container 2a through an opening 20 in a first end 30a of the container 2a. Preferably, the opening 5 of the container 2a is closed with the removable cover 6 prior to the placing of the composition P in the container 2a (e.g., by heat sealing, bonding, or similar technique). After attaching the removable cover 6 to the container 2a, the container 2a is positioned so that a base portion 4a is facing upward. In this position, the removable cover 6 preferably functions as a bottom of the container 2a. (See FIG. 4A.) For the embodiment of FIG. 3C, the reinforcing member 12 is placed in the container 2a prior to the placing of the composition P in the container 2a. Preferably, the reinforcing member 12 is placed in the container 2a prior to the closing of the opening 5 with the removable cover 6. When the container 2 is positioned so that the base portion 4a is facing up, the reinforcing member 12 is preferably proximal to the removable cover 6. The composition P is then placed in the container 2a through the opening 20 in the base portion 4a. (See FIG. 4B.) The container 2a is either partially or fully filled with the composition P, depending on the desired thickness of the patch 11b. When the patch 11c is formed in the container 2a, the reinforcing member 12 is preferably located in a portion 22 of the patch 11c proximal to the removable cover 6. After placing the composition P in the container 2a, the opening 20 is sealed with a cover member 23 (e.g. by bonding or heat sealing). (See FIG. 4C.) The cover member 23 is preferably an adhesive pellet. Preferably, the opening 20 is sealed prior to setting/gelling of the composition P. In one embodiment, the base portion 4a includes a second opening (not shown) to allow air heated from the composition P to escape from the container 2a after the opening 20 is sealed. As shown in FIG. 3C, the packaged patch system 1 is then positioned with the base portion 4a downward so that during the setting/gelling, the composition contacts the base portion 4a of the container 2a. In the embodiment of FIG. 3C, the reinforcing member 12 preferably migrates slightly in the direction of the base portion 4a so that the composition P forms a gelled matrix 34 about the reinforcing member 12. The reinforcing member 12 advantageously strengthens the patch 11b and prevents the patch 11b from becoming deformed (i.e., elongated) during use.

To use the packaged patch systems described above, a user first removes the removable cover 6. When the container 2 is flexible, the user slightly flexes (i.e., deforms) the base portion 4 of the container 2, 2a and removes the patch from the interior 3 of the container 2, 2a. Optionally, the user grasps a portion of the reinforcing member 45 extending from the patch (see FIG. 5) to facilitate removal of the patch. Thereafter, the user applies the patch to an outer surface of the body to provide a cosmetic and/or pharmaceutical treatment.

Advantageously, the patch can be manufactured in various shapes and sizes. For example, the patch can have a shape and size configured to fit around the eyes, on the forehead, on the nose, around the mouth, and/or on the cheeks or any other part of the body. Optionally, the container 2, 2a is made of an elastically deformable material (e.g., a thermoplastic elastomer) to facilitate deformation of the base portion 4 and removal of the patch.

EXAMPLE 1

The following are incorporated into 180 g of water:

3% by weight of gellan gum;

1% by weight of xanthan gum;

1% of wheat germ;

0.2% of preservative;

2% of orgasol; and 0.15% of essential oil of lavender.

A polyamide net is first placed in an interior of a polypropylene thermoformed container. Then, a composition at a temperature of about 90° C. is placed in the container so that the composition is at a depth of about 1 mm measured from a base portion of the container. Thereafter, the container is sealed by a heat-sealed removable cover.

After the user has removed the patch from the container, it is applied to the face for about 5 to about 60 minutes. Such a patch has a soothing, relaxing and tautening action.

EXAMPLE 2

The following are incorporated into 180 g of water:

2.5% by weight of gellan gum;

0.7% by weight of xanthan gum;

1% of alginate;

0.5% of ascorbic acid;

0.5% of preservative;

2% of ethanol; and

2% of SPF.

A polyamide net is first placed in an interior of a polyethylene injection-molded container. Then, a composition at a temperature of about 90° C. is placed in the container so that the composition is at a depth of about 1 mm measured from a base portion of the container. Thereafter, the container is sealed by a heat-sealed removable cover.

After the user has removed the patch from the container, it is applied to the face for about 5 to about 60 minutes. Such a patch has a soothing, lightening and levelling action.

EXAMPLE 3

The following are incorporated into 180 g of water:

2.5% by weight of gellan gum;

0.7% by weight of xanthan gum;

2% of flower extract;

0.5% of ethanol; and 0.5% of menthol crystals.

A polyamide net is first placed in an interior of a polyethylene terephthalate/aluminium/polyethylene complex thermoformed container. Then, a composition at a temperature of about 90° C. is placed in the container so that the composition is at a depth of about 1 mm measured from a base portion of the container. Thereafter, the container is sealed by a heat-sealed removable cover.

After the user has removed the patch from the container, it is applied to the face for about 5 to about 60 minutes. Such a patch has a refreshing and asepticizing action.

It will be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the following claims and their equivalents.

What is claimed is:

1. A cosmetic, pharmaceutical or dermatological patch for application to the skin, the patch comprising a reinforcement member and a composition comprising a hydrophilic gelling system in an aqueous phase, said hydrophilic gelling system comprising at least one gellan gum and at least one other hydrocolloid.

2. The patch according to claim 1, wherein said hydrophilic gelling system is less than 20% of the total weight of said composition.

3. The patch according to claim 1, wherein said gellan gum is present in an amount of at least 0.5% of the total weight of said composition.

4. The patch according to claim 1, wherein said gellan gum is present in an amount ranging from 2% to 15% of the total weight of said composition.

5. The patch according to claim 4, wherein said gellan gum is present in an amount ranging from 2 to 6% of the total weight of said composition.

6. The patch according to claim 1, wherein said at least one other hydrocolloid comprises at least one hydrocolloid chosen from: cellulose and its derivatives; seaweed extracts; seed extracts; plant exudates; microorganism exudates; fruit extracts; gelling agents of animal origin; amphiphillic polymers; water-soluble synthetic gelling polymers; terephthalic acid/isophthalic acid/sodium isophthalic acid sulfonate/glycol copolymers and silicon derivatives.

7. The patch according to claim 6, wherein said cellulose and its derivatives comprise cellulose and its derivatives chosen from carboxymethylcelluloses, hydroxypropylceluloses, methylcelluloses, hydroxypropylmethylcelluloses, hydroxyethylcelluloses and modified celluloses.

8. The patch according to claim 7, wherein said modified celluloses comprise modified celluloses chosen from celluloses modified by grafting of said cellulose's alkyl group.

9. The patch according to claim 6, wherein said seaweed extracts comprise seaweed extracts chosen from agar, carragheenans, and alginates.

10. The patch according to claim 6, wherein said seed extracts comprise seed extracts chosen from carob gums, guar gums and modified guar gums.

11. The patch according to claim 10, wherein said modified guar gums comprise modified guar gums chosen from guar gums modified by grafting the alkyl group of said guar gum.

12. The patch according to claim 6, wherein said plant exudates comprise plant exudates chosen from gum arabic, karaya gums, gum tragacanth and gatty gums.

13. The patch according to claim 6, wherein said microorganism exudates are xanthan gums.

14. The patch according to claim 6, wherein said fruit extracts are pectins.

15. The patch according to claim 6, wherein said gelling agents of animal origin comprise gelling agents of animal origin chosen from gelatins and caseinates.

16. The patch according to claim 6, wherein said synthetic water-soluble gelling polymers comprise synthetic water-soluble gelling polymers chosen from crosslinked polyacrylic acids.

17. The patch according to claim 6, wherein said silicon derivatives are synthetic hectorites.

18. The patch according to claim 1, wherein said at least one other hydrocolloid comprises at least one other hydrocolloid chosen from xanthan gum; cellulose derivatives, carob gum, and a modified guar gum.

19. The patch according to claim 1, wherein said at least one other hydrocolloid comprises at least one other hydrocolloid chosen from xanthan gum, carboxymethylcellulose and modified guar gum.

20. The patch according to claim 19, wherein said modified guar gum is hydroxypropyl guar.

21. The patch according to claim 1, wherein said at least one other hydrocolloid is present in an amount ranging from 0.5 to 10% of the total weight of said composition.

22. The patch according to claim 21, wherein said at least one other hydrocolloid is present in an amount ranging from 0.5 to 5% of the total weight of said composition.

23. The patch according to claim 1, wherein said aqueous phase is present in an amount ranging from 60 to 97% of the total weight of said composition.

24. The patch according to claim 23, wherein said aqueous phase is present in an amount ranging from 80 to 95% of the total weight of said composition.

25. The patch according to claim 1, wherein said composition further comprises at least one fatty phase.

26. The patch according to claim 25, wherein said at least one fatty phase comprises at least one oil.

27. The patch according to claim 25, wherein said at least one fatty phase further comprises a fatty substance.

28. The patch according to claim 26, wherein said at least one oil comprises at least one oil chosen from mineral oils, oils of plant origin, oils of animal origin, synthetic oils, silicone oils, fluorinated silicones and perfluorinated oils.

29. The patch according to claim 28, wherein said synthetic oils comprise synthetic oils chosen from fatty esters.

30. The patch according to claim 28, wherein said silicone oils comprise silicone oils chosen from volatile silicone oils, polymethylsiloxanes, polymethylphenylsiloxanes, polysiloxanes modified by fatty acids, fatty alcohols and polyoxyalkylenes.

31. The patch according to claim 27, wherein said fatty substance comprises a fatty substance chosen from fatty acids, fatty alcohols and waxes.

32. The patch according to claim 31, wherein said at least one fatty phase is present in an amount ranging up to 30% of the total weight of said composition.

33. The patch according to claim 32, wherein said at least one fatty phase is present in an amount ranging from 0.1 to 20% of the total weight of said composition.

34. The patch according to claim 33, wherein said at least one fatty phase is present in an amount ranging from 0.5 to 10% of the total weight of said composition.

35. The patch according to claim 26, wherein said composition further comprises at least one surfactant.

36. The patch according to claim 35, wherein said at least one surfactant comprises a surfactant chosen from nonionic, anionic, cationic and amphoteric surfactants.

37. The patch according to claim 36, wherein said at least one surfactant is present in an amount ranging from 0.05 to 8% of the total weight of said composition.

38. The patch according to claim 37, wherein said at least one surfactant is present in an amount ranging from 0.05 to 5% of the total weight of said composition.

39. The patch according to claim 1, wherein said composition further comprises at least one salt.

40. The patch according to claim 39, wherein said at least one salt comprises a salt chosen from monovalent, divalent and trivalent metal salts.

41. The patch according to claim 40, wherein said monovalent salts comprise monovalent salts chosen from alkali metal salts.

42. The patch according to claim 40, wherein said divalent metal salts comprise divalent metal salts chosen from alkaline-earth metal salts.

43. The patch according to claim 41, wherein said alkali metal salts are sodium salts.

44. The patch according to claim 42, wherein said alkaline-earth metal salts are calcium salts.

45. The patch according to claim 39, wherein said at least one salt comprises a salt made up from ions chosen from carbonates, bicarbonates, sulphates, glycerophosphates, borates, chlorides, nitrates, acetates, hydroxides and persulphates, salts of alpha-hydroxy acids, salts or fruit acids, and salts of amino acids.

46. The patch according to claim 45, wherein said salts of alpha-hydroxy acids comprise salts of alpha-hydroxy acids chosen from citrates, tartrates, lactates and malates.

47. The patch according to claim 45, wherein said salts of amino acids comprise salts of amino acids chosen from aspartates, arginates, glycocholates and fumarates.

48. The patch according to claim 39, wherein said at least one salt comprises at least one salt chosen from calcium, magnesium and strontium nitrates, calcium and magnesium borates, calcium, sodium, magnesium, strontium, neodymium and manganese chlorides, magnesium and calcium sulphates, and calcium and magnesium acetates.

49. The patch according to claim 39, wherein said at least one salt is present in an amount ranging from 0.01 to 2% of the total weight of said composition.

50. The patch according to claim 49, wherein said at least one salt is present in an amount ranging from 0.1 to 1% of the total weight of said composition.

51. The patch according to claim 1, wherein said composition further comprises at least one solvent chosen from primary alcohols, glycols, glycol ethers, and monoethylene, diethylene and triethylene glycols.

52. The patch according to claim 51, wherein said primary alcohols comprise primary alcohols chosen from ethanol and isopropanol.

53. The patch according to claim 51, wherein said glycols comprise glycols chosen from propylene glycol, butylene glycol, dipropylene glycol and diethylene glycol.

54. The patch according to claim 51, wherein said glycol ethers comprise glycol ethers chosen from monopropylene, dipropylene and tripropylene glycol alkyl ($C_1$–$C_4$) ethers.

55. The patch according to claim 51, wherein said at least one solvent is present in an amount ranging up to 10% of the total weight of said composition.

56. The patch according to claim 1, wherein said composition further comprises at least one active agent chosen from antioxidants, free-radical scavengers, moisturizers, bleaching agents, liporegulators, anti-acne agents, antiseborrhoeic agents, anti-ageing agents, softeners, anti-wrinkle agents, keratolytic agents, anti-inflammatories, refreshing agents, cicatrizing agents, vascular protective agents, antibacterials, antifungals, antiperspirants, deodorants, skin conditioners, desensitizing agents, immunomodulators, nourishing agents, moisture absorbers and sebum absorbers.

57. The patch according to claim 56, wherein said moisture absorbers comprise moisture absorbers chosen from cotton and polyacrylate.

58. The patch according to claim 1, wherein said composition further comprises at least one water-soluble active agent chosen from ascorbic acid and its biologically compatible salts, enzymes, antibiotics, components having a tautening effect, α-hydroxy acids and their salts, hydroxylated polyacids, sucroses and their derivatives, urea, amino acids, oligopeptides, water-soluble plant and yeast extracts, protein hydrolysates, hyaluronic acid, mucopolysaccharides, vitamins $B_2$, $B_6$, H and PP, panthenol, folic acid, acetylsalicylic acid, allantoin, glycyrrhetic acid, kojic acid and hydroquinone.

59. The patch according to claim 56, wherein said composition further comprises at least one liposoluble compound chosen from D-α-tocopherol, DL-α-tocopherol, D-α-tocopherol acetate, DL-α-tocopherol acetate, ascorbyl palmitate, vitamin F and vitamin F glycerides, vitamins D, vitamin $D_2$, vitamin $D_3$, retinol, retinol esters, retinol palmitate, retinol propionate, β-carotene, D-panthenol, farnesol, farnesyl acetate; jojoba and blackcurrant oils rich in essential fatty acids; keratolytic agents; asiatic acid, madecassic acid, asiaticoside, total extract of centella asiatica, β-glycyrrhetinic acid, α-bisabolol, ceramides; phytanetriol, milk sphingomyelin, phospholipids of marine origin, in polyunsaturated essential fatty acids, ethoxyquin; extract of rosemary, extract of melissa, quercetin, extract of dried microalgae and steroidal anti-inflammatories.

60. The patch according to claim 59, wherein said keratolytic agents comprise keratolytic agents chosen from salicylic acid, its salts and its esters, 5-(n-octanoyl)salicylic acid and its esters, and alkyl esters of α-hydroxy acids.

61. The patch according to claim 60, wherein said alkyl esters of α-hydroxy acids comprise alkyl esters of α-hydroxy acids chosen from alkyl esters of citric acid, lactic acid, and glycolic acid.

62. The patch according to claim 59, wherein said ceramides are 2-oleoylamino-1,3-octadecane.

63. The patch according to claim 1, said composition further comprising at least one setting retarder compound.

64. The patch according to claim 63, wherein said at least one setting retarder compound comprises at least one setting retarder compound chosen from salts.

65. The patch according to claim 1, wherein the patch is colored to facilitate visualization of impurities and/or residues taken out of the skin when the patch is applied to and/or removed from skin.

66. The patch according to claim 65, wherein the patch is colored by a pigment comprising a pigment chosen from synthetic, mineral, and organic pigments.

67. The patch according to claim 1, wherein the reinforcing member comprises a reinforcing member chosen from woven fabrics, nonwoven fabrics, and perforated films.

68. The patch according to claim 1, wherein the composition is coated on the reinforcing member to form the patch.

69. The patch according to claim 1, wherein the reinforcing member is embedded in the composition, said composition forming a gelled matrix about at least a portion of the reinforcing member to form the patch.

70. The patch according to claim 16, wherein said crosslinked polyacrylic acids are crosslinked via an alkyl chain.

71. The patch according to claim 67, wherein the reinforcing member is a net.

* * * * *